United States Patent [19]

Gear

[11] 4,090,129
[45] May 16, 1978

[54] STOPPED-FLOW REACTION APPARATUS UTILIZED IN CONJUNCTION WITH CONTINUOUS-FLOW RESISTIVE-PARTICLE COUNTING APPARATUS

[75] Inventor: Adrian R. L. Gear, Charlottesville, Va.

[73] Assignee: University of Virginia, Charlottesville, Va.

[21] Appl. No.: 763,631

[22] Filed: Jan. 28, 1977

[51] Int. Cl.² .................................... G01N 27/00
[52] U.S. Cl. ........................ 324/71 CP; 222/132
[58] Field of Search ............... 324/71 CP, 71 R; 222/132, 133, 137; 128/2 G

[56] References Cited

U.S. PATENT DOCUMENTS

| | | | |
|---|---|---|---|
| 3,554,037 | 1/1971 | Berg | 324/71 R X |
| 3,767,085 | 10/1973 | Cannon et al. | 222/137 X |
| 3,810,010 | 5/1974 | Thom | 324/71 CP |

OTHER PUBLICATIONS

"Improving Resolution in Coulter Counting by Hydro-Dynamic Focusing" by L. Spielman & S. L. Goren, Journal of Colloid and Interface Science 26, 175-182, (1968).

*Primary Examiner*—Rudolph V. Rolinec
*Assistant Examiner*—Vincent J. Sunderdick
*Attorney, Agent, or Firm*—Oblon, Fisher, Spivak, McClelland & Maier

[57] ABSTRACT

Stopped-flow reaction apparatus includes a dual drive syringe pump for pumping predetermined amounts of particles and reactants into a common reaction loop, the length of the latter, as well as the flow rate of the mixed solutions, determining the reaction time. The reacted solutions are then massively diluted, by means of a diluent supplied from another syringe pump, so as to freeze the state of reaction thereof and the diluted, non-reacting solution is then conducted to a continuous-flow, resistive particle counting apparatus.

10 Claims, 10 Drawing Figures

FIG. 10

STOPPED-FLOW REACTION APPARATUS UTILIZED IN CONJUNCTION WITH CONTINUOUS-FLOW RESISTIVE-PARTICLE COUNTING APPARATUS

The invention described herein was made in the course of work under a grant or award from the Department of Health, Education and Welfare and also partly funded by the Virginia Heart Association and thereby may be manufactured and used by or for the Government for governmental purposes without the payment of any royalties thereon or therefore.

BACKGROUND OF THE INVENTION

1. Field of the Invention

The present invention relates generally to continuous-flow, resistive-particle counting, and more particularly to stopped-flow aggregometry apparatus utilized in conjunction therewith in order to determine various parameters of blood platelets.

2. Description of the Prior Art

The following discussion refers to blood platelets. However, it must be emphasized that the principle of stopped-flow reactions is completely general. Any particles which can be detected by resistive-particle counters, and which react with other particles or chemicals, are potentially able to be analysed in the new apparatus.

Blood platelets play a key role in hemostasis, by providing various factors for the cascade pathway of coagulation, and in the direct formation of platelet plugs. They are also intimately involved in the important early events of atheroscherosis and in may bleeding disorders. In view of this, platelets having rightly attracted considerable attention towards understanding their formation in the bone marrow, their specific functions in the blood, and thei subsequent fate or destruction.

The development in the early 1960's of an optical, in-vitro test of platelet aggregation greatly helped to develop the fundamental biochemisty behind both normal and pathological platelet function. This test depends upon measuring the changes in the light transmittance of platelet-rich plasma (PRP) during aggregation wherein several characteristic phases occur. Initially, there is usually a small increase in the optical density for approximately 5-10 seconds after adding an aggregating agent, such as, for example, thrombin or adenosine diphosphate (ADP). This is referred to as the "shape change" phase and is associated with a disc-to-sphere transformation, during which time the platelets become covered with large numbers of projections or pseudopodia. Then, depending upon the concentration of the aggregating agent, the optical density of the PRP rapidly decreases as larger and larger platelet aggregates are formed. The second phase normally requires 1-2 minutes when ADP, adrenalin or thrombin are the aggregating agents, and an even longer time period, such as, for example, approximately 5 minutes, for collagen.

The optical tests therefore have an operational time scale of minutes, and it has proven difficult to obtain truly meaningful results concerning either the initial shape change or the rates of the extent of aggregation. Indeed, the theories of light scattering are complex, and the parameters of particle numbers volume and shape cannot be readily correlated with the changes in the optical density. These problems become particularly acute in view of a number of recent observations which show that many fundamental biochemical and structural events occur within seconds of initiating platelet aggregation.

By combining the same with continuous-flow techniques, successful techniques have been in clinical use for nearly 10 years, however, disadvantages nevertheless remain. In order to accomplish platelet counting, lysing agents must be used in order to remove the massive interference which would otherwise be caused by erythrocytes. For example, ammonium oxalate, in combination with a detergent, has been previously used, as has 2 M urea to lyse erythrocytes. A small disadvantage with such techniques, however, is that white cells are counted along with the platelets and have to be determined independently for a subsequent correction.

A major alternative to the optical sensing methods is resistive particle counting which has been a valuable analytical technique for the industrial, medical, and scientific communities for approximately 20 years, and which has provided information on particle numbers and particle size with respect to particles ranging in size from approximately 0.4–10$\mu$ or more in diameter. The more sophisticated apparatus have in fact been a considerable advance over earlier technology, providing up to seven parameters of clinical interest, mainly with regard to erythrocytes and white cells. In particular, clinical laboratories all over the world carry out enormous numbers of routine measurements of erythrocytes, white cell and blood platelets. Particle volumes are determined too, but this usually requires more ttime and expensive apparatus and is often not needed for medical diagnostic purposes. The advent of mini-computers has helped automate data reduction and has been very useful for calculating mean particle volumes and giving other statistical information from population histograms.

The major advantage of such apparatus is inherent in the original concepts where electrical information is available for determining both particle numbers and size, and potentially for shape too, with pulse-width analysis. The latter two parameters are of course not presently available with optical measuring systems. Other advantages are that pulse-height analysis is readily performed, and economical minicomputers provide capabilities of extensive data manipulation, aside from exhibiting great speed.

The technique of resistive counting is thus capable of providing the specific parameters of particle numbers and size, and thus has the potential of giving them during actual platelet aggregation. Several attempts have been made towards this end. For example, studies in the 1960's showed that ADP increased platelet volume by some 20 percent and it was considered that this reflected the disc-to-sphere transformation. Subsequently, independent techniques based on rapid centrifugation and the use of thrombocrits failed to reveal any increase in platelet volume. Therefore, the earlier resistive results were thought to stem from technical artifacts. An extensive recent investigation with the resistive technique has, however, shown that a highly-significant volume increase does occur in conjunction with the platelet shape change. This study took advantage of recent technical improvements in resistive counting and employed the basic conditions of the centrifugation procedures. It was found that both centrifugation and ethylenediaminetetraacetate (EDTA) caused platelets to swell and that EDTA also inhibited the change in volume. The net effect was to mask the true increase in platelet volume induced by ADP. Resistive counting has also been utilized to detect decreased amounts of single platelets during aggregation.

It seems clear then that resistive-particle counting can provide information on both platelet numbers and size during aggregation. However, several disadvantages inherent in the technique have prevented general application to platelet studies, particularly in terms of the very desirable goal of measuring initial rates of reaction. First, conventional resistive counting requires a sample of cells to be diluted some 100–1000 fold prior to analysis. This batch technique takes some 10–20 seconds before counting can be commenced. Secondly, at least 10 seconds of data accumulation are needed to obtain statistically-reliable numbers. Lastly, there has been no rapid way until very recently to measure particle volumes.

In addition, there are still other disadvantages of resistive counting. Simple clogging of the sensing orifice has been perhaps the major problem with all counters of such type, and one particular type of apparatus attempts to rectify such a problem through the provision of three orifice tubes each of white cells and erythrocytes, that is, six in all, with a corresponding duplication of circuitry. Comparison of the various data values from each then provides a means of detecting orifice blockage, however, the net result is complex and extremely expensive apparatus, which of course detracts from the inherent simplicity and ease of resistive-counter operation. Other approaches to the problem have also been utilized, such as, for example, a simple backflush plunger which is very valuable for cleaning nearly all blockages or the specific timing of the orifice flow rate has been another effective way to detect such problems. Still further, special redesign of the aperture tube, as disclosed in U.S. Pat. No. 3,746,976 to Hogg, wherein two orifices are used to minimize eddy currents, and therefore the generated electronic signals, has allegedly resulted in a self-cleaning orifice.

Other problems, however, have included poor resolution and skewed distributions of particles. The latter problem was apparently resolved, for example, with respect to erythrocytes, wherein the provision of longer orifice path lengths gave superior distibutions. Several recent approaches to the question of resolution demonstrate that it is often necessary to make complex modifications to the orifices. For example, Thom, as disclosed in U.S. Pat. No. 3,810,010, has designed a clever combination of two orifices, instead of one, wherein the particles are sucked out of the first orifice and surrounded by a sheath of particle-free electrolyte prior to their entry into the second sensing orifice. The improved resolution stems from the original concept of hydrodynamic focusing, however, Thom's apparatus is quite complex, and is dependent upon skilled glass-blowing and very precise geometries. In addition, due to the suction of the particles into the orifice together with the sheath of particle-free diluent, accurate counts of the detected particles are not obtained.

In U.S. Pat. No. 3,793,587 to Thom and Schulz, the apparatus disclosed therein serves to distinguish leucocytes from erythrocyte agglomerates, and to distinguish between two particles of equal volume but different shape. These goals are achieved by the use of two coaxial orifices of different path lenths, and a feed tube directed to the first orifice. As in U.S. Pat. No. 3,810,010, however, the same requires hydrodynamic sucking, which is a critical feature for success of the invention, and which, as noted hereinabove, draws in a quantity of particle-free diluent around the sucked particles through the first orifice. Consequently, the first orifice does not detect the true concentration of particles in the particle suspension.

Still further, a major disadvantage still remains in that intermittent and manual presentation of samples is still required. That is, individual liquid samples have to be handled and positioned over the sensing orifice prior to each analysis. In addition, relatively-large equantities of blood (1.3 ml) have to aspirate into the machine, mainly to flush away previous samples, and after appropriate dilution, the sample is subject to a static count. On the other hand, flow-counting techniques do have an inherent advantage over that static resistive approach in that they are more flexible in that multiple samples are able to be run in a continuous train towards the sensing zone. In addition, specific manipulations, such as reagent addition, are readily performed on the samples before analysis. Nevertheless, further improvement and/or refinement of such apparatus, and the technique associated therewith is desired.

SUMMARY OF THE INVENTION

Accordingly, it is an object of the present invention to provide a new and improved resistive-particle counting apparatus.

Another object of the present invention is to provide a new and improved resistive-particle counting apparatus of the continuous-flow type.

Still another object of the present invention is to provide a new and improved continuous-flow resistive-particle counting apparatus which is able to measure properites of particles previously unattainable with conventional resistive techniques or apparatus.

Yet another object of the present invention is to provide a new and improved continuous-flow resistive-particle counting apparatus which is utilized in conjunction with stopped flow mixing apparatus.

Still yet another object of this invention is to provide a new and improved continuous-flow resistive-particle counting apparatus which is able to measure the rate and extent of various particle reactions, such as, for example, blood-platelet aggregation.

A further object of the present invention is to provide a new and improved continuous-flow resistive-particle counting apparatus wherein the stopped-flow aggregometry mixing apparatus permits platelets to aggregate for short, but defined, periods of time.

A yet further object of the present invention is to provide a new and improved stopped-flow aggregometry apparatus which facilitates the understanding of the earliest events in platelet functioning, specifically within 5 seconds of initiating aggregation, or more particularly, wherein the parameters of particle numbers and size are able to be analyzed within 2 seconds of stopping the reaction.

A still further object of the present invention is to provide a new and improved stopped-flow aggregometry and continuous-flow resistive-particle counting apparatus which has the ability to measure the initial reates of aggregation in terms of platelets reacting as well as the increase in volume of the same during the shape change phase thereof.

A still yet further object of the present invention is to provide a new and improved stopped-flow aggregometry apparatus which has the ability to selectively vary the reaction times of the samples being tested.

An additional object of the present invention is to provide a new and improved continuous-flow resistive-particle counting apparatus which is able to analyze any number of samples without physical manipulations of the same within the vicinity of the sensing zone orifice.

A yet additional object of the present invention is to provide a new and improved continuous-flow resistive-particle counting apparatus which is able to directly measure particle size, as well as absolute numbers, of a large number of samples, such as, for example, the quantitating and sizing of blood particles.

The foregoing and other objects are achieved in accordance with the present invention through the provision of stopped-flow reaction apparatus which includes a dual drive syringe pump for pumping predetermined amounts of, for example, platelet rich plasma (PRP) and reactant or aggregating agent into a common reaction loop, the length of the latter, as well as the flow rate of the mixed solutions, determining the reaction time. The reacted solutions are then massively diluted, by means of a diluent supplied from another syringe pump, so as to freeze the reaction thereof, and the diluted non-reacting solution is then conducted to a continuous-flow, resistive particle counting apparatus.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts throughout the several views, and wherein.

DETAILED DESCRIPTION OF A PREFERRED EMBODIMENT

Figure 1:
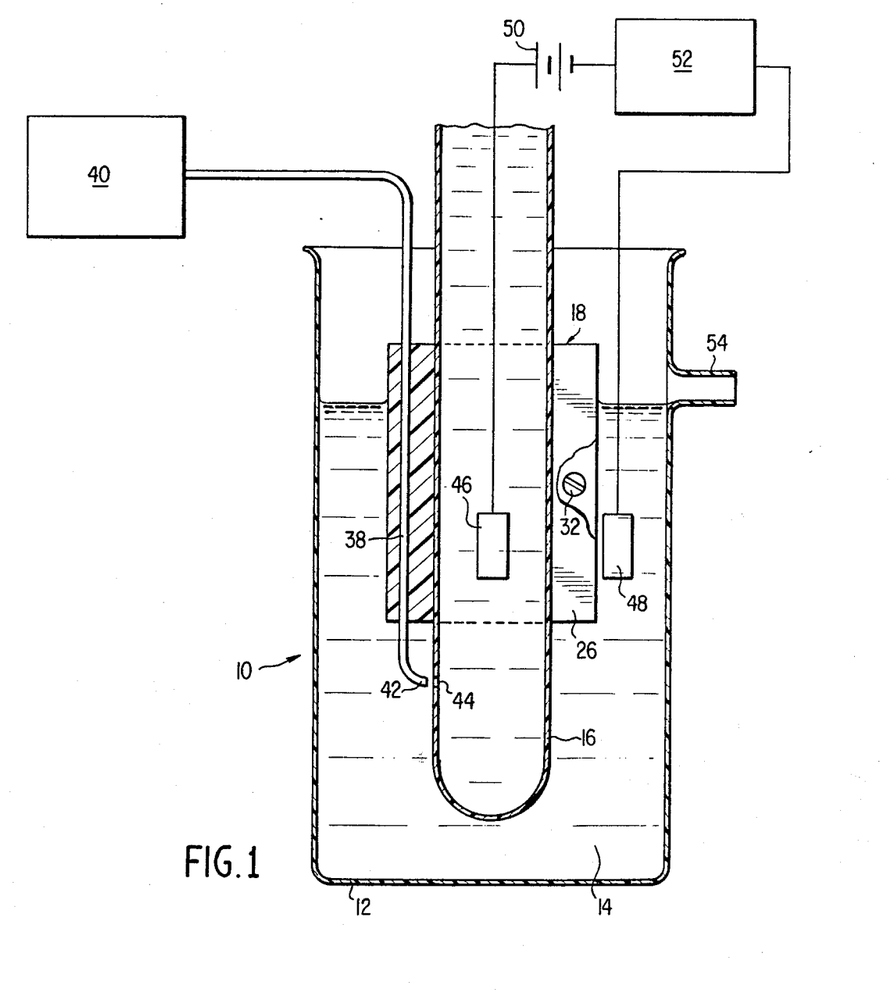
FIG. 1 is a schematic view, in a vertical plane, of a continuous-flow resistive-particle counting apparatus constructed in accordance with the present invention and showing its cooperative parts.
Figure 2:
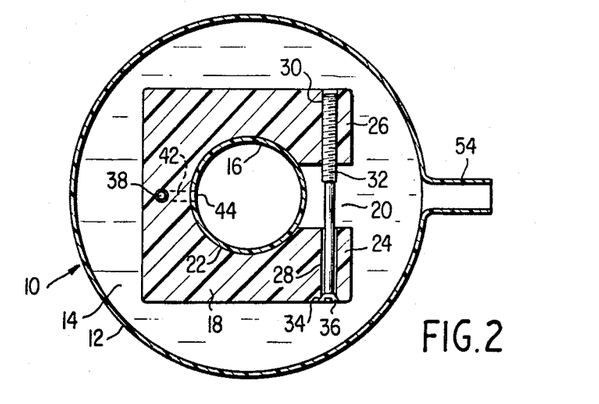
FIG. 2 is a schematic view, in a horizontal plane, of the apparatus of FIG. 1.

Referring now to the drawings, and more particularly to FIGS. 1 and 2 thereof, the continuous-flow, resistive-particle counting apparatus to be utilized in conjunction with the stopped-flow aggregometry apparatus of the present invention is generally indicated by the reference character 10 and is seen to include a container or breaker 12 within which is disposed a bulk electrolyte 14. An orifice tube 16, which has the general configuration of a conventional test tube, is centrally disposed within a supporting block 18 so as to be coaxially disposed therewith. The block 18 has substantially the configuration of a rectangular parallelepiped, with a longitudinal opening 20 defined within one side thereof serving to define an open area which renders the block C-shaped in horizontal cross-section, as best seen in FIG. 2, the block therefore also having a cylindrical opening 22 within which orifice tube 16 is disposed.

Block 18 may be fabricated of Lucite and the arms or legs 24 and 26 of block 18, which serve to define opening 20, are respectively provided with aligned openings or bores 28 and 30 within which a suitable fastening member, such as, for example, a bolt 32, may be disposed. Bore 28 of block leg 24 is non-threaded and the other end 34 thereof has a conical configuration which matingly engages the head 38 of bolt 32, while bore 30 is threaded so as to threadedly engage the threaded end portion of bolt 32. An injection tube 38, which may be fabricated of stainless steel (20 gauge), is fixedly embedded, along a longitudinal portion thereof, within block 18 so as to extend substantially parallel to orifice tube 16. The upstream end of tube 38 is fluidically connected to a pumping system, generally indicated by the reference character 40, while the downstream end of tube 38 projects below block 18 and is curved radially inwardly with, for example, a 2 mm radius of curvature, so as to define an injection jet 42.

Orifice tube 16 is provided with a sensing orifice 44 within a side-wall portion thereof, and the jet 42 is of course disposed within the vicinity of, and oriented towards, orifice 44, with the end of the tube 38 disposed approximately 1 mm from orifice 44. Still further, as a result of the provision of fastener 32, and the selective loosening or tightening of the same, block 18 may be moved vertically, or pivoted about the longitudinal axis thereof, relative to orifice tube 16 so as to selectively accurately position jet 42 relative to orifice 44. It has been determined that the injection tube 38, and more particularly jet 42, does not have to be disposed directly in front of sensing orifice 44, and such relative disposition provides the useful capability of direct unhindered viewing of the orifice, for the important and routine checking of orifice cleanliness or blockages, by means of conventional microscope systems built into commercial conventional resistive particle counters.

As can also be appreciated from FIG. 1, a first electrode 46 is fixedly disposed within orifice tube 16 so as to be coaxial therewith, while a second electrode 48 is fixedly disposed within container 12 within the vicinity of, or adjacent to, block 18 and at a vertical level corresponding to that of electrode 46. The electrodes are of course disposed within an electrical circuit which includes a power source 50 and suitable, conventional particle measuring, detecting, and displaying apparatus generally indicated by the reference character 52. Container 12 is further provided with an overflow conduit 54 which is fluidically connected to a waste container, not shown, for accumulating the excessively pumped or waste bulk electrolyte. Further attributes of the continuous-flow resistive-particle counting apparatus are disclosed in Applicant's co-pending application Ser. No. 763,630, entitled "Continuous-Flow Resistive-Particle Counting Apparatus Utilized In Conjunction With Continuous-Flow Mixing Apparatus".

As is also noted within the above-identified co-pending application, all analyses were carried out with a commercial resistive particle counter which was used in conjunction with an 8K minicomputer, a magnetic-tape unit for the storage of programs and experimental data, and an oscilloscope for visualising the data accumulation. The minicomputer controls counter function and serves directly as a pulse-height analyzer and data reducer, and a hard-copy output of the data may be accomplished by means of a Teletype.

The results to be presented are for the specific system of platelets and platelet aggregation. However, it must be emphasized again that the stopped-flow reaction system in conjunction with the continuous-flow modification of resistive-particle counters is entirely general. Any appropriate combination of particles and reactants could be analyzed.

For nearly all the results to be reported, a 48 $\mu$ sensing orifice 44 was used, although a 30 $\mu$ orifice may also be employed with no difference in system performance. Platelet sizing was by reference to standard latex particles, which were 2.02 $\mu$ in diameter and were fabricated of polyvinyltoluene.

Two parameters were routinely measured with the foregoing apparatus, first, simply particle counts, such as, for example, the number of particles passing through the sensing orifice per unit of time (usually 10 seconds), and second, the log mean platelet volume. The latter results from the fact that a logarithmic amplifier processes the sensing-zone pulses before transmission to the minicomputer for pulse-height analysis. In order to obtain corrected counts, standard coincidence corrections were applied, and coupled with the orifice flow rate and sample dilution, such gave the number of particles in the original solutions. Normal statistics were applied to the experimental data, and if necessary the Student's test may be used to test the significance of a given sample.

Figure 3:
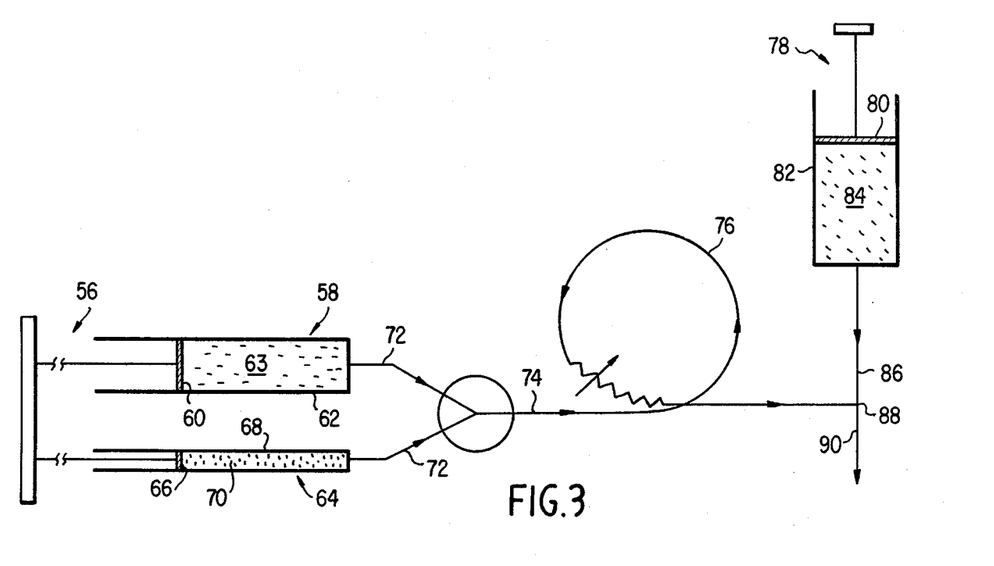
FIG. 3 is a schematic view of the stopped-flow aggregometry apparatus constructed in accordance with the present invention and showing its cooperative parts.

Referring now to FIG. 3, the stopped-flow aggregometry apparatus of the present invention is seen to include pumping apparatus 40 which comprises a dual-drive syringe pump, generally indicated by the reference character 56, which consists of a first, syringe pump 58 having a first piston 60 which is operatively disposed within a first syringe container 62 within which is housed a predetermined amount of platelet-rich-plasma (PRP) 63, and a second, syringe pump 64 having a second piston 66 which is operatively disposed within a second syringe container 68 within which is housed a predetermined amount of saline (0.154 M NaCl) or platelet-poor plasma (PPP) 70 containing a predetermined amount of an aggregating agent, such as, for example, adenosine diphosphate (ADP). The solutions are then conducted through separate tubing members 72 having, for example, a 0.8 mm I.D. and 1.6 mm O.D., and are subsequently conducted through a common reaction tube member 74.

A critical feature for successful platelet aggregation is to have vigorous mixing between the platelet-rich-plasma and the platelet-poor-plasma, or saline, containing aggregating agent, and this is achieved by fabricating the reaction tubing of a tubular member having a 0.3 mm I.D. so as to generate the necessary shear forces, the extent of the reaction between the PRP and reactant solutions being determined by both the length of tubing 74 and the flow rate of the solutions therethrough, as more particularly noted hereinbelow, it being apparent that tubing 74 includes a variable length reaction loop 76. The tubing and the connectors are preferably made of Teflon, and the Y junctions are preferably fabricated of nylon in order to achieve a minimal amount of dead volume.

A single-drive syringe pump, generally indicated by the reference character 78, is also provided within the stopped-flow aggregometry system and is seen to include a piston member 80 operatively disposed within a container or cylinder 82 within which is disposed 60–120 ml of 0.154 M NaCl solution, the supply or amount of the solution within container 82 being selectively varied between either 60 ml or 120 ml by utilizing a single 60 ml syringe, or alternatively, operatively connecting two 60 ml syringes together in parallel, the latter serving to provide the longest possible time of continuous dilution operation. Three-way stopcocks, not shown, connect the syringes by means of suitable tubing to a saline reservoir for refilling purposes, and the diluting syringe pump may be of the electronically-variable motor type.

In accordance with the foregoing, the PRP and reactant solutions are massively diluted some 100–500 fold by means of the saline solution within container as a result of the same being conducted through additional tubing 86 which is interconnected with the end of reaction tubing 74 at a juncture 88, and the diluted solution is then conducted by means of further tubing 90, to the continuous-flow resistive-particle counting apparatus of FIGS. 1 and 2, and more particularly to the injection tubing 38. As noted hereinabove, as the PRP and PPP solutions are conducted through reaction tubing 74 having a precise, predetermined length and at a predetermined flow rate, an exact reaction time is established. Furthermore, as a result of the provision of the large volume of diluting agent 84, platelet aggregation within the reaction loop and tubing is effectively stopped whereupon the diluted, non-reacting platelets are then conducted to the injection tube 38 and jet 42 for particle counting operations.

It should be noted that successful operation of the complete, stopped-flow system requires that the pumping speeds of both syringe pumps 56 and 78 be set so as to fulfill two needs, the first being that the dual-channel pump 58 driving the PRP and aggregating agent into the common reaction loop must work fast enough so as to provide reaction times as short as 1 second, and generate sufficient mixing so as to ensure aggregation, and second, the diluting syringe pump 78 should completely stop platelet aggregation and at the same time give an appropriate dilution for accurate counting by the resistive-particle counter.

The following settings have proved suitable for meeting the above objectives. The dual-channel pump 56 was adjusted so as to deliver 2.76 $\mu$l per sec down the common reaction loop 76, and this flow rate is for the two 1 ml syringes combining their outputs. The reaction loop was always calibrated to determine its exact internal diameter and an appropriate length was then established so as to give the desired reaction times. Between 5–20 cms of the teflon tubing covered the range of 1-approximately 30 seconds, the slower times being simply obtained by decreasing the pump speed through four to five incremental steps, each being 1.4-fold slower than the preceding one.

The diluting syringe pump 78 was usually operated so as to deliver 200 $\mu$l per second (12 ml per min), and this imparts an injection velocity at the sensing orifice 44 of some 0.7 m per second, a value which ensures reliable counting performance. When platelet counts became too high for suitable coincidence correction, the diluting syringe pump was run at 400 μl per second. The final dilution factors over the complete range of platelet flow rates varied from approximately 70–500-fold.

Figure 4:
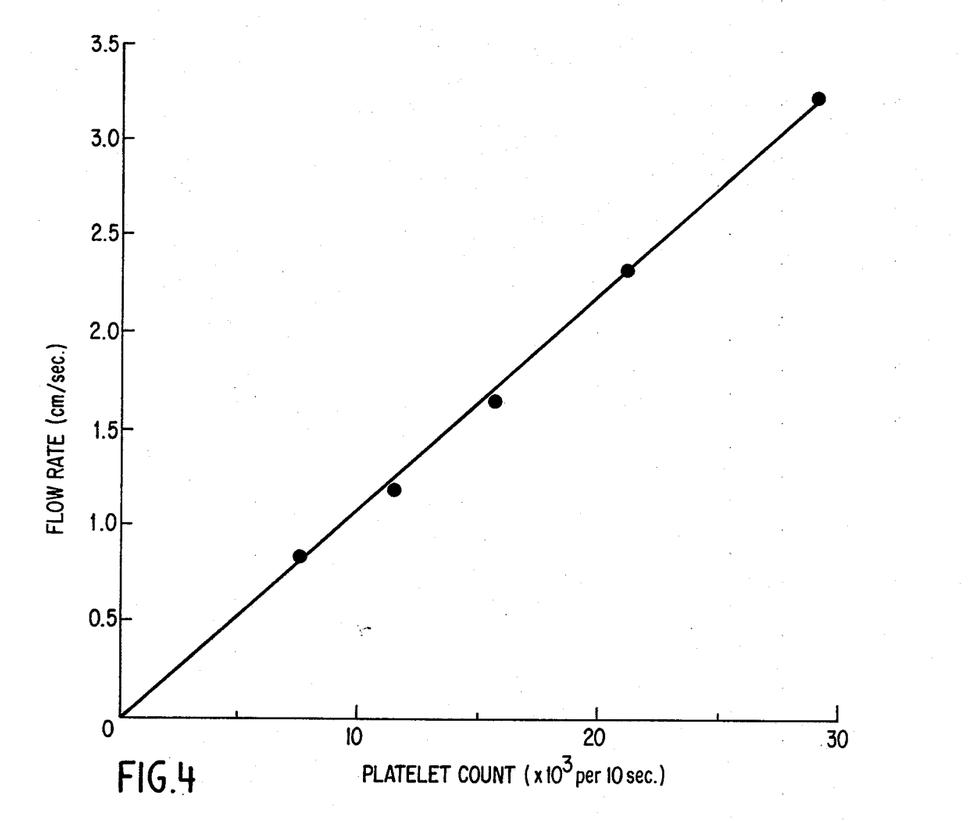
FIG. 4 is a graphical plot showing the interrelationship between the solution flow rate and the platelet counts.

An example of the performance of the combined systems is illustrated in FIG. 4 wherein the expected linear relationship between observed platelet counts and flow rate through the reaction loop is illustrated. Platelet-rich-plasma (PRP) was placed in a 1 ml plastic syringe 62, and 0.154 M NaCl in the second syringe 68. The syringes were driven by means of syringe pump 56 and their outlets fed into the common tube 74 of 0.31 mm I.D., and 5.3 cm long. The flow rate through this tubing was varied in discrete steps by controlling the output of the syringe pump 56, and dilution of the PRP - saline mixture suitable for resistive counting was performed by the second syringe pump 78 driven at the rate of 12 ml per min. The results are expressed as observed counts per 10 seconds of analysis time, corrected for coincidence, and are the means of at least four data accumulations.

It will now be useful to describe the procedures followed to measure actual rates of platelet aggregation. Human venous blood was obtained from forearm veins and collected into one-ninth its volume of acid-citrate-dextrose (ACD) solutions to give a final citrate concentration of 0.38 percent (W/V) trisodium citrate. Three short centrifugations of the ACD-whole blood mixture were then carried out to obtain the PRP. The first and second were for 1200 g min and the third was for 2000 g min, and at each step the supernatants were gently aspirated off and the erythrocyte-rich pellet centrifuged further. The combined supernatants were maintained in plastic centrifuge tubes and stored at room temperature (20°), and care was taken to carry out all tests with the PRP as soon as possible, since it is known that storage for more than a couple of hours begins to result in decreased efficiencies of aggregation. In general, function tests were complete within 4 hours of drawing the blood.

The platelet-rich plasma is then placed in one of the 1 ml syringes 62 and 0.154 M NaCl in the other syringe 68. The diluting syringe 82 is primed with saline and both pumps are started at the speeds indicated hereinabove. Prior to this, the resistive-particle counter is calibrated with respect to the standard particles, and set to analyze for 10 seconds, calculate mean sizes for about 7 seconds, and repeat the cycle automatically. If sizing is not required and simple platelet numbers are all that is desired, then a brief modification of the computer program is made. In this case only about ½ a second is taken to print the data on the Teletype. Also for particle counters without a minicomputer, counting can be carried out very satisfactorily for a given volume passing through the sensing orifice, or per unit time.

The dual-channel syringe pump 56 is next slowed down by one step in speed as soon as three or more 10-second data accumulations have been recorded. Usually, five different pumping speeds are sufficient to cover the reaction rate in question. For ADP as the aggregating agent, reaction times from 1.5 to 6 seconds allow accurate calculation of initial rates of reaction. The purpose of the first run is to establish control values for each pumping speed, against which will later be compared the counts obtained in the presence of the aggregating agent. Typical raw data of a control run, as printed out on the Teletype, is shown in Table 1.

TABLE 1

| Typical Raw-Data Output During Stop-Flow Analysis | | | |
|---|---|---|---|
| Velocity in Stopped-Flow Loop (cms/sec) | Reaction Time (sec) | Counts (per 10 sec) | Log Mean Volume ($\mu^3$) |
| 2.41 | 2.9 | 15,637 | 5.61 |
|  |  | 15,673 | 5.61 |
|  |  | 15,667 | 5.48 |
| 1.72 | 4.1 | 11,522 | 5.61 |
|  |  | 10,885 | 5.61 |
|  |  | 11,443 | 5.61 |
| 1.23 | 5.8 | 8,049 | 5.61 |
|  |  | 8,019 | 5.48 |
|  |  | 7,967 | 5.48 |

Platelet-rich plasma was placed in the stop-flow apparatus and the syringe-pump speed varied. After dilution with 0.154 M NaCl the platelets were counted and sized through the continuous-flow jet of the resistive-particle counter. The results are given as the raw data, uncorrected for coincidence, and the log mean platelet volume. The log mode and median volumes have been omitted for clarity. Only three pumping speeds are given for clarity. The values would then be averaged at each speed and corrected for coincidence.

The next step in the operating procedure is to fill the second, 1 ml syringe 68 with aggregating agent and prime the input line down to the mixing point of tubes 72. The pumps and resistive counter are started and the same sequence of flow rates as for the control is followed. By comparing the coincidence-corrected data against the control values at each pumping speed or reaction time, the percentage of single platelets remaining in solution can be determined. A single plot of these percentages versus time then allows the efficiency of aggregation to be calculated. This is expressed by the percentage of single platelets aggregating per second.

It should be emphasized here that accurate control of temperature in the reaction loop is essential for reproducible results. This has been achieved in two ways. The simplest is to have a beaker insulated with polystyrene foam and fill it with 37° water prior to each run with the aggregating agent. During a complete run of 4 – 5 minutes, the temperature drops by approximately 1°.

In connection with a detailed study to be discussed hereinbelow, the influence of temperature on the rate of aggregation was also accomplished by means of a circulating, refrigerated water bath hooked up to the reaction beaker. This arrangement gave control within 0.2°. It was found by measurement with thermocouples that the 20 – 30 seconds of pre-incubation for the inflowing PRP and saline or aggregating agent was sufficient to achieve full equilibration to the reaction temperature.

In order to follow the volume increase associated with the shape-change phenomenon, a slightly different arrangement of the apparatus is necessary. The reason for this is that the largest platelets aggregate first leaving behind very small ones. Since the aggregates are excluded from sizing by the counter, the mean platelet volume begins to decrease very rapidly after the initial increase. Rate measurements are thus not practicable with the normal system.

The way to circumvent this problem is to block platelet aggregation without inhibiting the shape change. This has been achieved in the past by using EDTA, but EDTA has recently been shown to inhibit the extent of the volume increase associated with the shape change.

Consequently, the present approach has been to avoid the use of EDTA and add the aggregating agent along with the diluting saline used for the resistive counting. Aggregation cannot occur in dilute solution, however, the shape change appears normal. This technique is similar to that used by earlier workers in resistive-particle counting.

The procedure adopted to determine the rate of volume increase is as follows. The aggregating agent, for example 5 $\mu$M ADP, is added directly to the saline in the diluting syringe 82. The second, 1 ml syringe 68 in the dual-channel pump 56 is simply filled with saline. The pumps are started and the reaction time is now determined by the flow rate through the length of the 0.8 mm ID teflon tubing between the point of dilution and the continuous-flow jet. Therefore, different reaction times are achieved by varying the pumping speed of the diluting syringe 82 or by changing the length of the inlet tube. The flow rate must fall within the range of approximately 40 down to 5 ml per min for reproducible sizing or counting. Results are printed out on the Teletype as the log mean, mode and median platelet volumes.

Figure 5:
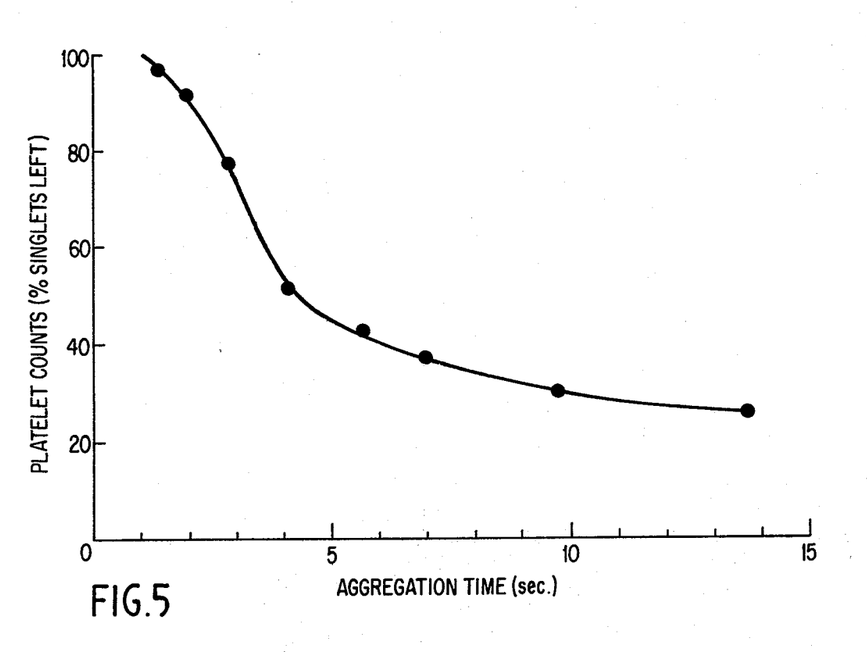
FIG. 5 is a graphical plot showing the interrelationship between the platelet counts and the aggregation time.

A typical experiment showing the influence of different reaction times on the numbers of single platelets detected by the resistive counter is illustrated in FIG. 5, the concentration of ADP being 5 $\mu$M in the stopped-flow loop, while that of the platelets was 158,000 per $\mu$l. The different aggregation times were obtained by varying the pump speed to give flow rates from 4.7 down to 1.23 cm per sec, and also by changing the tube length for the three slowest aggregation times. Results are expressed as the percentage of single platelets remaining in solution, and the temperature was 37°.

Two important features are evident in the time course of aggregation. First, there is small delay of 1 – 2 seconds before significant reaction occurs. This behaviour has been observed with nearly all preparations of PRP, that is less than 10 percent have shown no delay in the onset of aggregation. It has also been found that higher concentrations of ADP cause a significant decrease in the onset time. Thus, 10 $\mu$M ADP gave a mean value of 1.17 ± 0.77 sec, and 5 $\mu$M ADP gave 1.54 ± 0.92 sec; for eight different PRP preparations, plus or minus 1 standard deviation. Using Student's $t$ test for paired data the difference between the two ADP values was significant to $p < 0.05$. The onset time was estimated from where the tangent to the aggregation slope intercepted the 100 percent line. An additional observation should also be made. After the PRP was stored for more than 4 to 5 hours, the onset time actually decreased; often to less than 1 second.

The second notable feature about aggregation measured by stopped-flow aggregometry is its speed. About 50% of all platelets in this particular experiment formed aggregates by 4 seconds after adding the ADP. The mean 50% reaction time for 13 different PRP preparations was 5.1 ± 1.0 sec. This observation is in sharp contrast to classical aggregometry wherein a 50% reaction, as measured optically, does not occur until between 30 – 120 seconds. Therefore, the stopped-flow system records events almost an order to magnitude faster than the optical technique. The actual rate of aggregation for the particular preparation of PRP used for FIG. 5 was 20% of the platelets reacting per second.

An important goal in studying platelet functions is to be able to relate the efficiency of aggregation to a given experimental or pathological situation. Since the blood platelet count may vary by a factor of four and still be within the normal range, it is necessary to be sure that differences in experimental values for platelet efficiency are not caused by fluctuating platelet numbers. Therefore, a mechanism should exist for normalizing functional efficiency. For optical aggregometry, a reasonable linear relationship exists between both the extent and rate of reaction with numbers and it has been suggested that simple normalization is a valid and useful procedure.

Figure 6:
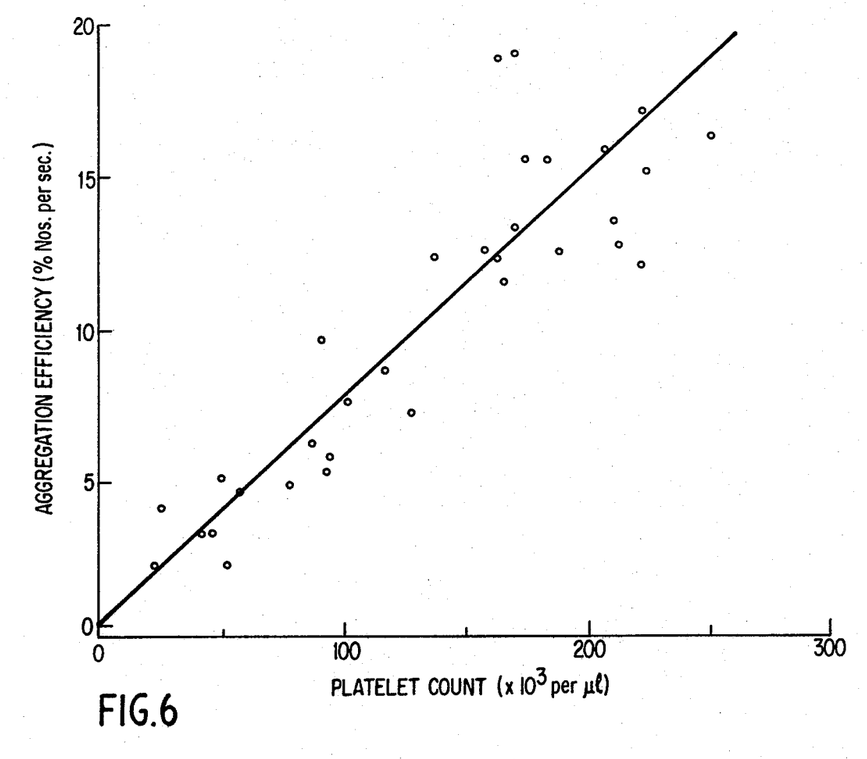
FIG. 6 is a graphical plot showing the interrelationship between the aggregation efficiency and the platelet count.

In view of this, a number of experiments have been carried out with the stopped-flow apparatus. The results given in FIG. 6 reveal that efficiency depends linearly upon the platelet count (correlation coefficient, 0.9000). These findings underly the rationale that the PRP does not have to be adjusted to a standard platelet count prior to efficiency testing. Efficiencies can be determined immediately, saving experimental time, and only normalized later to 200,000 platelets per mm$^3$. The latter refers to the concentration in the stopped-flow, reaction loop, while that in the PRP syringe would be double. The mean efficiency of aggregation for the set of data presented in FIG. 6 is 15.1% of the platelets reacting per second at 200,000 particles per mm$^3$.

It might be mentioned at this point that the aggregating-agent syringe 68 may be filled with either 0.154, M NaCl or platelet-poor plasma. Experiments with ADP revealed no significant difference in aggregation efficiencies.

Figure 7:
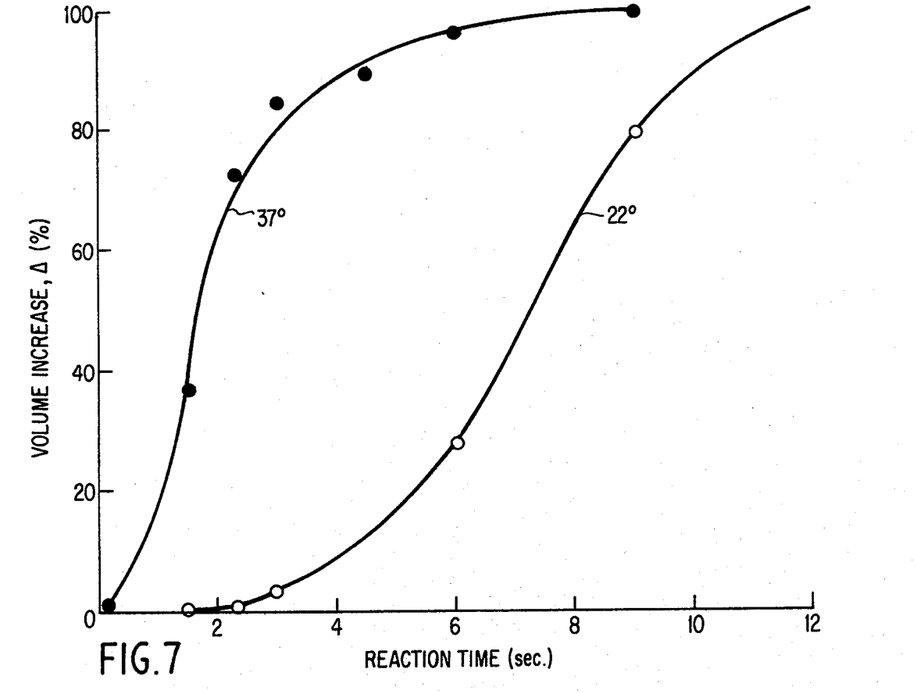
FIG. 7 is a graphical plot showing the interrelationship between platelet volume and reaction time at two temperatures, 22° and 37°.

The second major parameter measured by resistive counters is that of volume. Illustrated in FIG. 7 are two experiments wherein 5 $\mu$M ADP was used to induce the shape change. In distinction to the normal way of measuring platelet aggregation, the reaction loop or time is now related to the distance between the point of dilution and the sensing orifice 44. This technique prevents aggregation but allows the shape change to occur. The different reaction times were obtained by varying the pumping rate of the diluting ADP syringe. The syringe pump containing the PRP was run at a constant rate of speed, and results are expressed as the log-mean platelet volume in $\mu^3$, the temperatuure being 22° for the (O) plot, and for the second experiment (•), 37°. The change in volume is expressed as a percentage to allow direct comparison of the two sets of data. For example, the maximal increase in log-mean platelet volume for the 22° experiment was 0.9 $\mu^3$; this value is then set as 100%, and all other values are considered to be a percentage of it. The log-mean platelet volume before adding the 5 $\mu$M ADP was 6.01 $\mu^3$.

These experiments clearly demonstrate the feasibility of using the stopped-flow approach for studying the rate of volume increase associated with the platelet shape change. One feature of the results is worth noting here, that is, there is a marked influence of temperature on the rate of reaction. At 37° the half-time was 1.8 seconds after adding the ADP, some 3 seconds before 50% aggregation occurred as measured by the decrease in platelet singletons a noted in FIG. 5, and this will be discussed further hereinbelow.

Having shown the basic operating conditions and results of the stopped-flow system, it is desirable to apply the new technique to a more general study. Of particular interest is the relationship between the rate of platelet aggregation and the concentration of aggregating agent. This has relevance to both mechanisms of normal platelet function and pathological conditions, such as in atherosclerosis, wherein changes in sensitivity to aggregation agent have been noted.

Figure 8:
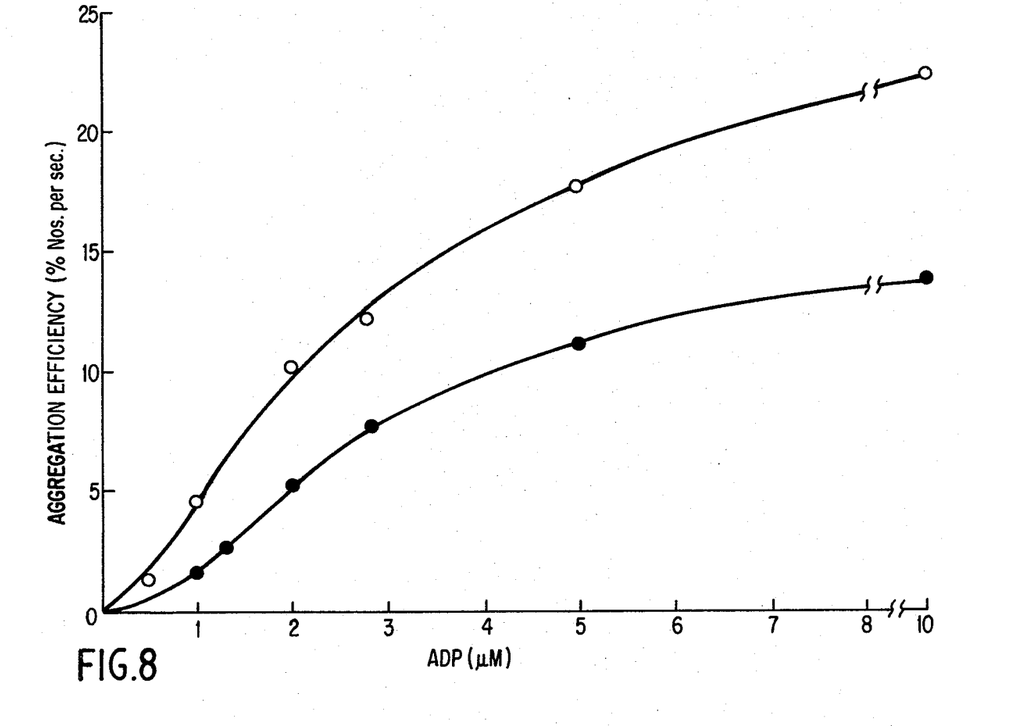
FIG. 8 is a graphical plot showing the interrelationship between the aggregation efficiency and the ADP concentration.
Figure 9:
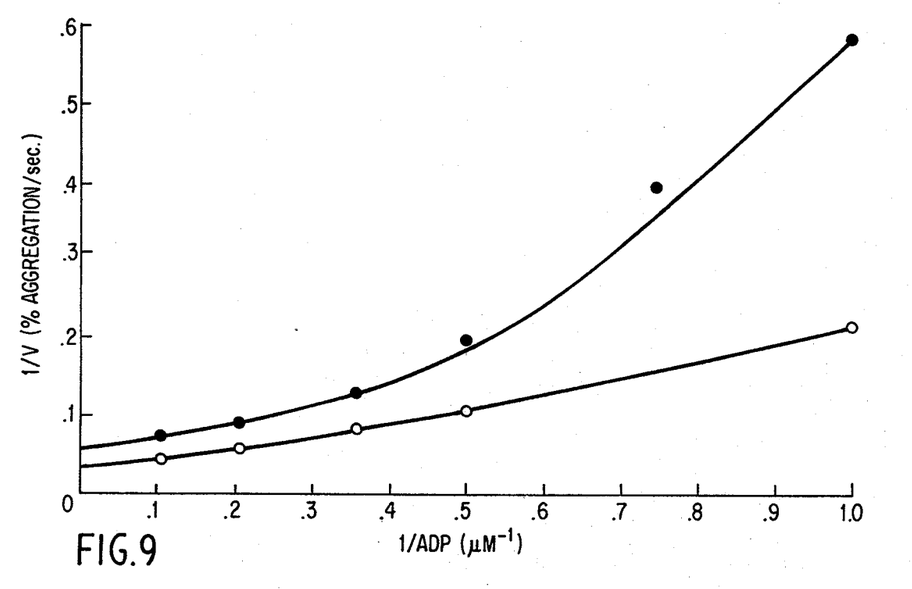
FIG. 9 is a graphical plot showing the interrelationship between the reciprocal values of efficiency of the platelet reaction and the ADP concentration.

Accordingly, a number of experiments have been carried out on the efficiency of aggregation as a function of the ADP concentration, and these are summarized in FIG. 8 which is a direct, velocity versus concentration plot, and FIG. 9, the corresponding Michaelis-Menten analysis wherein the data given in FIG. 8 has been transformed into a double-reciprocal plot and used to calculate values for 'Vmax', the maximal rate of aggregation, and 'Ka', the activation constant for ADP. A separate Hill plot was needed to calculate the values for 'n', the cooperativity constant, and the designations (•, O) are the same as in FIG. 8. Two sets of data are shown, the first set being derived from seven individuals, who might be called "normals", and the second from two persons who platelets were much more active. The stop-flow apparatus was used to follow the rates of platelet aggregation induced by 0.5 up to 10 $\mu$M ADP. Aggregation efficiencies are normalized to 200,000/$\mu$l of particles in the reaction loop, and are expressed as the percent of platelets aggregating per second. The temperature was 37° for the (•) plot of mean efficiencies for seven individuals; and the (O) plot is the average of two persons demonstrating a much higher V max and less sigmoidicity of ADP. More particularly, three major parameters can be derived from the kinetic analysis 'V max', the maximal efficiency of individual platelets reacting per second, and normallized to 200,000 platelets per mm$^3$; 'Ka', the apparent activation constant, which is the concentration of aggregating agent giving half-maximal efficiency, or Vmax/2; and lastly, 'n', the cooperatively or Hill coefficient.

The kinetic data is given in Table 2.

TABLE 2

Kinetic Data From ADP-Induced Aggregation

| Individual | K a ($\mu$M ADP) | V max (%/sec) | Hill coefficient, 'n' |
|---|---|---|---|
| Normals (7) | 3.4 ± 2.2 | 16.0 ± 5.4 | 2.02 ± 0.70 |
| "Hyperaggregable" (2) | 3.4 | 31.3 | 1.16 |

The original raw data summarized in FIGS. 6, 7 have been used to derive the above values for: 'K$^a$', the concentration of ADP to induce the half-maximal rate of aggregation; 'V max', the maximal rate of aggregation; and finally 'n', the Hill coefficient which is a measure of the cooperativity in the process of aggregation. The number of individuals tested is given in brackets. It is intriguing that the Ka of 3.4 $\mu$M ADP is the same for both sets of individuals, and is similar to values based on the optical aggregation test. However, the major distinction is in the V max; 16.0 ± 5.4% per second for the "normals", versus 31.3% per second for two "hyperaggregable" individuals. A second difference is that the former platelets exhibited better control to ADP as evidenced by a higher Hill coefficient 'n' of 2.02 ± 0.7 versus 1.16. In other words, below a certain concentration of ADP they are relatively unreactive; above it, their efficiency increases in a cooperative manner.

Although the data is derived from a small sample, it suggests that valuable information is contained in a Michaelis-Menten analysis of platelet aggregation by stop-flow kinetics. For really effective evaluation a much broader sample of normal individuals, together with known disorders of platelet function, is needed.

The fact that temperature had a dramatic effect on the rate of the volume change, as seen in FIG. 7, was noted hereinabove. A more complete aggregation study has been carried out and a similar strong influence found, the results being expressed in the form of an Arrhenius plot and shown in FIG. 10, wherein platelet-rich plasma was induced to aggregate in the stop-flow apparatus in the presence of 5 $\mu$M ADP. The temperature of the reaction loop was varied from 42° down to 18°, and the results are expressed as an Arrhenius plot, and are the means from the PRP from five individuals.

Figure 10:
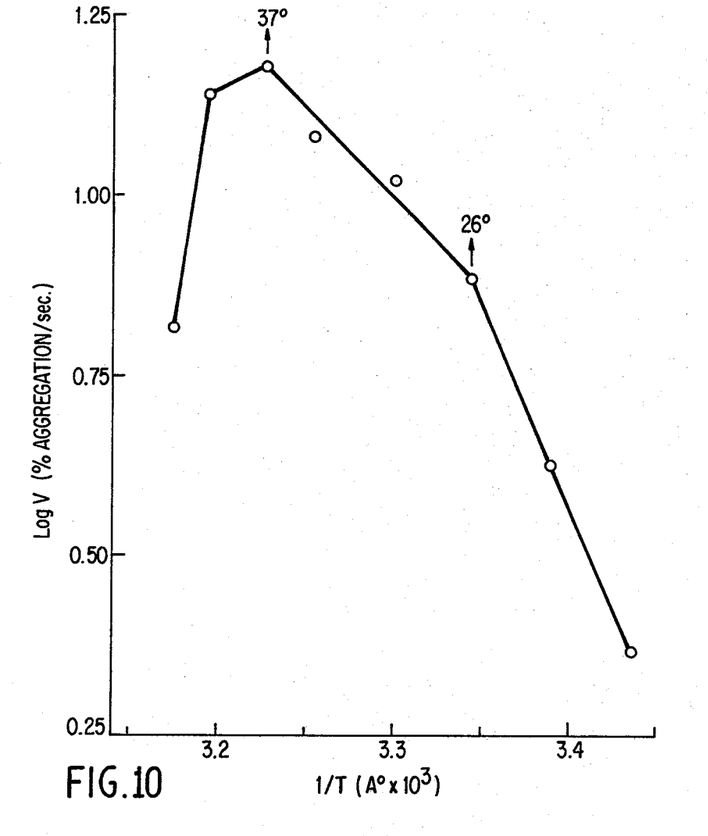
FIG. 10 is a graphical plot showing the interrelationship between the rate of aggregation and temperature.

Several points are to be noted first beint that it is intriguing that there is a relatively narrow temperature optimum from about 36°-40°, and that above 40°, the rate of aggregation falls off precipitously. A second finding is that the Arrhenius plot is non-linear below 37°, there being a distinct "break" within the vicinity of 26°. The energy of activation above 26° was 11.4 k cals per mole, and below 26°, 26.5 K cals per mole. Experiments on the rate of aggregation measured optically gave the same general results, namely, rapid inactivation at temperatures above 40°, as well as exhibiting the 26° "break". However, absolute values for the activation energies were significantly lower ($p < 0.05$, $n = 5$). This may stem from the differences in what events the two techniques actually monitor.

It should be emphasized here that short pre-incubation times before testing were used in both the stopped-flow and classical-aggregometry techniques. The former was about 20 - 30 seconds, and the latter was standardized at 3 minutes. Consequently, it is felt that decreased platelet aggregation at the higher temperatures does not result from substrate depletion or cell breakdown, but is rather a true influence of temperature on the reaction mechanism.

Thus, it may be seen that two established techniques, namely, resistive counting and stopped-flow systems, may be combined to produce a new and valuable approach to studying platelet function. The most useful test to data has involved the optical, in-vitro aggregometer. However, the test is difficult to interpret in the absolute terms of platelet members or size, and cannot provide information on highly significant structural and biochemical events occurring within seconds of initiating aggregation. It is particularly these early events that the new technique of stopped-flow aggregometry can investigate, and allow calculation of initial reates of platelet reaction as numbers or size. The results presented herein reveal that aggregation is extremely rapid, that the shape change with its associated increase in volume is 50% complete in less than 2 seconds, and aggregation in terms of the disappearance of platelet singletons is 50% complete within 5 seconds.

The continuous-flow, injection system forms a key link in allowing the resistive-particle counter to analyze directly the output of the stopped-flow reaction loop as it provides for continuous analysis by the resistive counter of particle numbers and size within 2 sconds of stopping platelet aggregation at the end of the reaction loop. This factor is important. Preliminary investigations showed that partially-aggregated platelets begin to disaggregate 20 - 30 seconds after dilution for resistive counting, and in some cases were completely dissociated into singlets by 5 - 15 min.

The second part of the system is the stopped-flow combination of syringe-pumps and connecting tubing. The heart of this is the teflon reaction loop of approximately 0.3 mm internal diameter. It might be mentioned that earlier prototypes using polyethylene tubing worked equally well. What is novel about platelet aggregation here is that no special mixing chamber, or stirring bars are required to ensure reaction. Simple mixing of the aggregating agent with the PRP at the inlet, together with the shear forces generated by the fluid flow in the narrow-bore tubing, are sufficient to cause the aggregation. Indeed, the physical conditions of the 0.2 – 0.4 mm internal diameter and about 1 – 4 cm per sec flow rate approach those found in small arteries. This probably means that the very rapid reactions actually measured in conjunction with the present invention apparatus really do reflect what might happen in vivo. Using the resistive-counter flow system, it then opens up many fields for investigation: effects of flow rate, tubing diameter, different aggregating agents, platelets from patients with bleeding disorders, diabetes or the various hyperlipidemias. Preliminary experiments have already been carried out with adrenalin and thrombin as aggregating agents. The former is about one-half as active as ADP, with some 30 percent of the platelets reacting by 6 seconds. Thrombin on the other hand has a longer onset time than ADP, about 4 seconds, but then it appears to cause aggregation with almost the same efficiency.

The influence of platelet aging, or in-vitro storage, is another area where the stopped-flow system has potential. Preliminary studies have shown that efficiency decreases by about 20 percent between 2 – 6 hours after venupuncture (initial value 14.8 ± 4.0% of platelets reacting per second; final value 12.0 ± 2.3%; $p < 0.1$, $n = 4$), and additional work can be performed, especially to investigate the influence of citrate concentration, plasma pH, and storage time on both the efficiency of aggregation and the rate and extent of volume increase. As evidenced by the optical aggregation test, these factors are known to have significant effects on threshold concentrations of aggregating agents, initial velocities of reaction and their extent. Another area which must be studied is the variability, for a given individual, of his platelet's functional efficiency with time. Since only 5 ml whole blood is required for a function test, this is quite feasible. An indication of potential results comes from one individual who was tested on two successive days. His PRP counts were 317,000 and 312,000 per mm$^3$, and the respective raw efficiencies were 19 and 20% of platelets reacting per second.

The speed with which aggregation and the volume increase occur are most intriguing. Little hint of this is evident in the optical aggregation tests although recent modifications using polarized light do provide more accurate analysis at the 5-second peak in optical shape change. However, no specific parameters can be measured. It was observed in FIG. 5 that 50 percent aggregation took place within approximately 5 seconds, while less than 2 seconds were required for a 50 percent change in volume as seen in FIG. 7. These findings correlate well with results based on a totally-different technique, that of rapid-fixation, electron microscopy, wherein distinct shape change and pseudopodia formation by means of shadow-cast, electron micrographs of rapidly-fixed platelets at 1 to 2 seconds after addition of ADP has been shown. This time scale corresponds with the volume increase demonstrated by stopped-flow aggregometry as seein in FIG. 7. In addition, within 3 – 6 seconds after ADP, numerous inter-platelet bridges were visualized and this observation could parallel the rapid change in platelet singletons (50% reaction at 5 seconds) found in accordance with the present invention. Consequently, the new technique does appear to measure true, initial events in the physiology of platelet aggregation. It offers the specific advantage over other techniques in being able to provide actual rates and extents of reaction as the defined parameters of platelet numbers and volume.

The observation that the volume increase had a shorter lag time, less than 1 second, and a rate of reaction three times that of aggregation, is entirely consistent with the known sequence of physiological events during aggregation. That is, platelets change shape with the formation of pseudopodia prior to the adhesion of particles to each other. Aggregation is therefore a complex sequence of events, and some of the other findings with stopped-flow aggregometry could well prove valuable for a more detailed understanding. Detailed analysis of the influence of temperature revealed several interesting features as seen in FIG. 10, the occurrence of a "break" in the Arrhenius plot at 26°, with a very high activation energy below 26° (26.5 K cals per mole), might well be correlated with the observation by others that the platelet release reaction does not occur below 27°. This could rationalize the lower activation energy about 26° by saying that the products of the release reaction, namely $Ca^{++}$, serotonin and adenine nucleotides, facilitate the aggregation process and lower the activation energy. Two tests of this hypothesis appear viable. First, an inhibotor of the release reaction, such as aspirin, might be expected to abolish the 26° "break", and second, if the Hill coefficient '$n$' reflects the efficiency of the release reaction and the consequent cooperative or autocatalytic nature of aggregation, then a detailed Michaelis-Menten analysis at 25° and not the 37° of the present study, should cause the value of '$n$' to decrease to unity.

Some general applications of stopped-flow aggregometry should also be noted. In this study a resistive counter was used to characterize platelets emerging from the reaction loop. The fact that aggregation does occur with excellent efficiency means that any other technique could really be applied for studying the initial phases of platelet function. For example, it should be possible to stop aggregation with fixative and carry out electron-microscopy; or, the efflux from the reaction loop might be frozen or treated with perchloric acid to prevent any further biochemical events. Early metabolic changes could then be examined in detail.

A significant goal of future research must be to understand how platelet function is related to atherosclerosis and some of the bleeding disorders. The brief mention of finding some individuals with what could be called hyperaggregable platelets and lacking poor control as evidenced by a low Hill coefficient suggests that stopped-flow aggregometry could prove valuable in a study of patients known to have a serious risk of vascular disease. To have a rapid and precise assay of aggregation efficiency would serve several important clinical needs, such as for example, as noted, in the knowledge of the efficacy of platelet packs used in correction of bleeding problems; second, in the diagnosis of many hemostasis disorders; and to assess whether platelet function is adequate before surgery, especially since many drugs such as aspirin can be troublesome.

Based on present experience, it would seem that a key routine and rapid assay of platelet function lies in having a simple way of switching the stop-flow, reaction loops. Therefore, it may be proposed to set up six reaction loops, each of the appropriate length (or reaction time) and connected by means of two, 6-way rotary valves to the outflow of the diluting syringe. In this way it should be possible to switch loops thereby varying the extent of platelet aggregation and thereby determine the actual rate of aggregation. The present technique uses changing flow rates through one loop, and is somewhat slower to carry out.

It is also to be noted that while the above disclosure utilized ADP, other platelet aggregating agents, such as adrenalin, collagen and thrombin can also be used. These reagents are often characterized by longer aggregation times, and consequently, different reaction loops will have to be constructed to cover the appropriate reaction times.

Lastly, commercial value of the present invention will normally be in hospital and research laboratories for measuring blood-platelet aggregation. It should be emphasized, however, that the general principles outlined above do not apply to blood platelets alone. They are just as relevant to any system where changes in particle numbers, size, or both might occur. Therefore other potential uses could involve following interaction between leucocytes and bacteria, platelets with bacteria or erythrocytes with Rickettsiae.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Stopped-flow, reaction apparatus for use in conjunction with continuous-flow resistive-particle counting apparatus, comprising:
    means for housing a predetermined amount of particles to be counted;
    means for housing a predetermined amount of a reactant;
    means for simultaneously injecting said particles and said reactant into a common reaction loop having a predetermined length, at a predetermined flow rate so as to facilitate reaction of said particles by said reactant;
    means for housing a diluent, the amount of said diluent relative to that of said particles and reactant being in the range of 70 – 500 : 1;
    means for injecting said diluent into said reaction loop so as to massively dilute the same and thereby stop the reaction;
    continuous-flow resistive particle counting apparatus; and
    means fluidically connecting said reaction loop to said counting apparatus so as to supply said non-reacting solution to said counting apparatus.

2. Apparatus as set forth in claim 1, wherein:
    said reaction loop is a tubular member having an inside diameter within the range of 0.2 – 0.4 mm.

3. Apparatus as set forth in claim 1, wherein:
    said flow rate is within the range of 1–4 cm/sec.

4. Apparatus as set forth in claim 1, wherein:
    said simultaneous injecting means is a dual-drive syringe pump.

5. Apparatus as set forth in claim 1, wherein:
    the length of said reaction loop is variable so as to vary the reaction time.

6. Apparatus as set forth in claim 1, wherein said continuous-flow resistive-particle counting apparatus comprises:
    container means for housing a bulk electrolyte;
    an orifice tube closed at the lower end thereof and having a sensing orifice defined within a side wall portion thereof, a portion of said electrolyte thereby being disposed within said tube;
    a first electrode disposed within said electrolyte disposed within said orifice tube;
    a second electrode disposed within said bulk electrolyte disposed within said container;
    electric circuit means including a power source, electrically connecting said first and second electrodes;
    fluid injection means disposed within said container at a position radially outwardly of said orifice tube and within the vicinity of said sensing orifice of said orifice tube for forcefully injecting a fluid jet of said diluted reacted particles to be counted toward said sensing orifice at a flow rate which is at least ten-fold the normal flow-rate of said electrolyte from said container through said sensing orifice and into said orifice tube; and
    means disposed within said electrical circuit for counting said particles passing through said sensing orifice.

7. Apparatus as set forth in claim 6, further comprising:
    a holding block disposed about said orifice tube and having a selectively variable diameter so as to selectively grasp or release said orifice tube and thereby render said block selectively fixed about said tube, or vertically movable or pivotable about the longitudinal axis of said tube, respectively;
    means for controlling the diameter of said block; and
    said injection means includes an injection jet tube fixedly disposed within said block, said injecting tube having an injection jet defined within the end thereof disposed within said vicinity of said sensing orifice,
    whereby the disposition of said injection jet relative to said sensing orifice is adjustable.

8. Apparatus as set forth in claim 7, wherein:
    said block is substantially C-shaped in horizontal cross-section; and
    said means for controlling the diameter of said block is a threaded fastener threadedly engaged within the arms of said block defining said C-shaped portion thereof.

9. Apparatus as set forth in claim 6, further comprising:
    overflow means defined within said bulk electrolyte container.

10. Apparatus as set forth in claim 1, wherein:
    said particles are blood platelets.

* * * * *